United States Patent [19]

Lauer et al.

[11] 4,273,711
[45] Jun. 16, 1981

[54] PROCESS FOR THE PREPARATION OF 4-HYDROXYCARBAZOLE

[75] Inventors: Karl Lauer, Schriesheim; Einhart Kiegel, Mannheim, both of Fed. Rep. of Germany

[73] Assignee: Boehringer Mannheim GmbH, Mannheim, Fed. Rep. of Germany

[21] Appl. No.: 163,253

[22] Filed: Jun. 26, 1980

[30] Foreign Application Priority Data

Jul. 14, 1979 [DE] Fed. Rep. of Germany ....... 2928483

[51] Int. Cl.$^3$ .......................................... C07D 209/88
[52] U.S. Cl. .................................................... 260/315
[58] Field of Search ........................................ 260/315

[56] References Cited

U.S. PATENT DOCUMENTS 3,892,766  7/1975  Zinnes .................................. 260/315

FOREIGN PATENT DOCUMENTS 2240599  2/1974  Fed. Rep. of Germany .

Primary Examiner—Henry R. Jiles
Assistant Examiner—R. W. Ramsuer
Attorney, Agent, or Firm—Sprung, Felfe, Horn, Lynch & Kramer

[57] ABSTRACT

The present invention provides a process for the preparation of 4-hydroxycarbazole by the dehydration of 1,2,3,4-tetrahydro-4-oxocarbazole, wherein the reaction is carried out in aqueous alkaline solution, using Raney nickel as catalyst.

7 Claims, No Drawings

PROCESS FOR THE PREPARATION OF 4-HYDROXYCARBAZOLE

This invention relates to an improved process for the preparation of 4-hydroxycarbazole. This compound is an important starting material for the preparation of pharmacologically-active carbazole derivatives as shown, for instance by West German Pat. No. 2,240,599.

There are several possibilities for the synthesis of 4-hydroxycarbazole:

1. From bromonitrobenzene and iodoanisole:

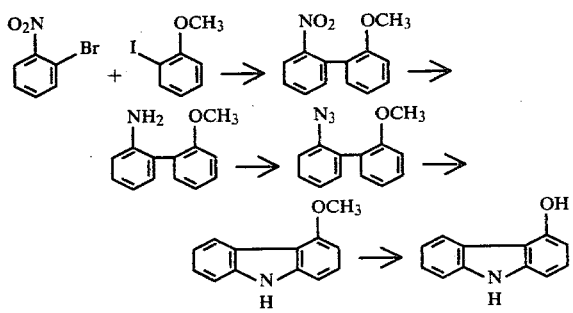

However, this process is not very suitable for the economic preparation of 4-hydroxycarbazole because the starting materials are very expensive and the process gives rise to considerable process-technical difficulties.

2. From chloronitrobenzene via dinitrobiphenyl:

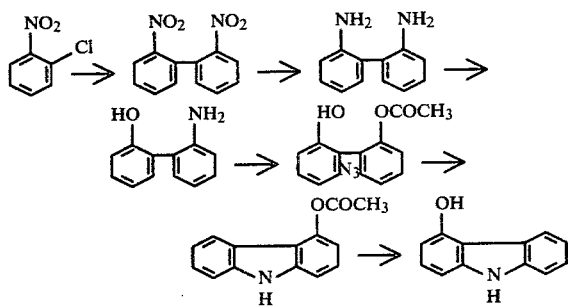

This six-step synthesis also suffers from considerable disadvantages. As a result of the dangerousness of one of the intermediate stages in which hydrazoic acid is used, special precautionary measures are necessary. The other expenses involved are also great so that the overall costs are considerable.

Thus, for solving the problem of being able to prepare comparatively large amounts of 4-hydroxycarbazole, it was necessary to develop a process which is economic and can be carried out on a technical scale. This process is illustrated by the following equation:

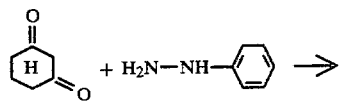

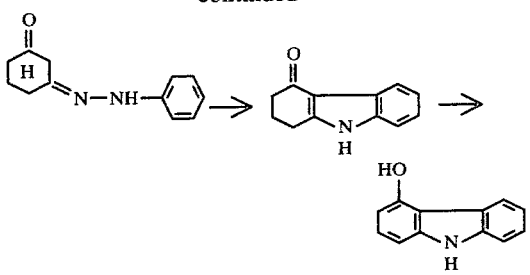

Cyclohexane-1,3-dione is reacted with phenylhydrazine to give cyclohexane-1,3-dione monophenylhydrazone which is converted by a Fischer rearrangement into 1,2,3,4-tetrahydro-4-oxo-carbazole (see Annalen, 278, 39/1894; J.C.S., 1951, 700), dehydration of which gives 4-hydroxycarbazole. Of decisive importance for the economic carrying out of this process is the discovery of a suitable method of dehydration or of a suitable dehydration catalyst.

Several of the methods of dehydration or aromatization known from the literature were tested, for example:
(a) dehydration by bromination/dehydrobromination
(b) dehydration with sulphur
(c) dehydration with lithium chloride/cupric chloride (see Tetrahedron Letters, 1977, 821)
(d) dehydration with pyrolusite
(e) dehydration with lead dioxide
(f) dehydration with chloranil.

However, all these methods gave unsatisfactory results.

Furthermore, the dehydration of tetrahydrooxoindole with palladium-carbon has also been described (see J. heterocyclische Chemie, 14, 71/1977; and Chim. Ther., 1970, 279) but considerable amounts (up to 50% by weight) of the expensive palladium-carbon catalyst, referred to the starting material, are necessary and the reaction only proceeds well in high boiling point solvents, such as cymol.

We have now, surprisingly, found that the dehydration of 1,2,3,4-tetrahydro-4-oxo-carbazole already takes place at 100° C. in aqueous, alkaline solution with the use of Raney nickel as catalyst. This was not to have been expected because the starting material scarcely dissolves in aqueous alkali. Furthermore, the small amount of carbazole formed is also surprising.

Thus, according to the present invention, there is provided a process for the preparation of 4-hydroxycarbazole by the dehydration of 1,2,3,4-tetrahydro-4-oxocarbazole, wherein the reaction is carried out in aqueous alkaline solution, using Raney nickel as catalyst.

For carrying out the process, the 1,2,3,4-tetrahydro-4-oxocarbazole is taken up in an aqueous alkali solution, preferably in an aqueous solution of potassium or sodium hydroxide. The aqueous alkali solution is used in a 4 to 8 fold and preferably in a 5 to 6 fold stoichiometric amount, referred to the amount of 1,2,3,4-tetrahydro-4-oxocarbazole used. It is advantageous to work with approximately 2 N aqueous alkali solution. It is also advantageous to work in an atmosphere of an inert gas, for example under nitrogen. The reaction is carried out under reflux boiling and takes about 50 to 70 hours. In order to isolate the product, the alkaline reaction solution is separated off from the catalyst and acidified, the product precipitating out in a form which can be centrifuged off.

The economic aspect of the process according to the present invention is especially favorable since the production costs are only about one tenth of those of the method described above under (2).

The following Example is given for the purpose of illustrating the present invention:

EXAMPLE

Chemicals:
60 kg. potassium hydroxide
30 kg. 1,2,3,4-tetrahydro-4-oxocarbazole
21 kg. Raney nickel catalyst, moist (type B 113 B) semi-concentrated hydrochloric acid.

Into a clean 1200 liter $V_4A$ stainless steel apparatus, there are successively introduced 450 liters of water, 60 kg. analytically pure potassium hydroxide pellets and 30 kg. 1,2,3,4-tetrahydro-4-oxocarbazole, while ensuring that the potassium hydroxide pellets have dissolved before introducing the 1,2,3,4-tetrahydro-4-oxocarbazole.

The apparatus is then closed, evacuated twice and decompressed again with nitrogen. The catalyst is introduced and the apparatus again flushed with nitrogen. While stirring, the reaction mixture is then boiled under gentle reflux. The reaction time is about 60 to 64 hours.

When the reaction is finished, the reaction mixture is cooled to ambient temperature and filtered. The strongly alkaline solution is then adjusted to pH 12.1 (pH meter) with semi-concentrated hydrochloric acid. Precipitated 1,2,3,4-tetrahydro-4-oxocarbazole (about 2 kg.) is filtered off with suction.

The suction filtered solution is again placed in the 1200 liter $V_4A$ stainless steel apparatus and then, while stirring, the pH is adjusted to 1 by the slow addition of semi-concentrated hydrochloric acid. The precipitated product is centrifuged off and washed free of acid with water. Subsequently, it is dried at 60° C. in a vacuum drying cabinet. There are obtained about 24 to 25 kg. 4-hydroxycarbazole with a melting point of 163°–164° C.

The following procedure is used for the preparation of the 1,2,3,4-tetrahydro-4-oxocarbazole used as starting material:

1. Cyclohexane-1,3-dione monophenylhydrazone.
Chemicals:
40.0 kg. cyclohexane-1,3-dione
38.7 kg. phenylhydrazine
550 liters ethanol
3.4 kg. activated charcoal (Brilonite Fx pure).

40 kg. Cyclohexane-1,3-dione are dissolved in 250 liters of water at 20° C. in a 1200 liter enamelled apparatus. The apparatus is thereafter evacuated twice and decompressed with nitrogen. A solution of 38.7 kg. phenylhydrazine in 500 liters of water is allowed to run in via an inlet vessel at an internal temperature of 20° to 25° C. within the course of 4 hours. Initially, about 50 liters are allowed to run in in the course of 20 minutes, followed by stirring for 30 minutes. Crystallization is tested for by means of a sample. The total amount is then added thereto in the course of 4 hours. Subsequently, the reaction mixture is further stirred for 3 hours. The sandy-like cyclohexane-1,3-dione monophenylhydrazone obtained is centrifuged off and washed with 350 liters of water.

The crude product thus obtained is dried at 60° C. in a circulating air drying cabinet, the yield obtained being 70 kg. The dried crude product is recrystallized from the 6.7 fold amount (about 500 liters) of ethanol, with the addition of 3.4 kg. of active charcoal. After drying at 60° C., there are obtained 46 kg. of cyclohexane-1,3-dione monophenylhydrazone with a melting point of 187°–189° C.

2. Cyclization.
Chemicals:
22 kg. cyclohexane-1,3-dione monophenylhydrazone
110 kg. zinc chloride
130 liters glacial acetic acid
ethanol
active charcoal (Brilonite Fx pure)

130 Liters of glacial acetic acid and 110 kg. of zinc chloride are introduced into a dry and clean 500 liter enamelled apparatus. Thereafter, 20 liters of glacial acetic acid are distilled off at atmospheric pressure. At an internal temperature of 60° to 70° C., 22 kg. of cyclohexane-1,3-dione monophenylhydrazone are introduced. The reaction mixture is heated to 90° to 110° C. at atmospheric pressure with steam and the temperature then maintained with a hot water circulation. The reaction is exothermal: if the internal temperature increases above 110° C., the reaction mixture should be briefly cooled. The contents of the apparatus are kept for a total of about 4 hours at a temperature of 90° to 100° C. After 4 hours, the reaction mixture is cooled to 75° to 80° C. and the hot solution stirred into 1100 liters of water, whereafter stirring is continued for 1 hour. The crude product is centrifuged off and washed substantially free of chloride with about 500 liters of water. After drying in a circulating air drying cabinet at 60° C., there are obtained about 17 kg. 1,2,3,4-tetrahydro-4-oxocarbazole. The product is recrystallized from ethanol (about 1:13) (clear, dark solution), with the addition of 10% Brilonite Fx pure. The yield is 12 to 13 kg. and the product has a melting point of 220°–221° C.

It will be understood that the specification and examples are illustrative, but not limitative of the present invention and that other embodiments within the spirit and scope of the invention will suggest themselves to those skilled in the art.

What is claimed is:

1. Process for the preparation of 4-hydroxycarbazole which process comprises dehydrating 1,2,3,4-tetrahydro-4-oxocarbazole in aqueous alkaline solution using a Raney nickel catalyst.

2. Process as claimed in claim 1 wherein the aqueous alkaline solution is employed in an amount four to eight times the stoichiometric amount of 1,2,3,4-tetrahydro-4-oxocarbazole.

3. Process as claimed in claim 2 wherein the aqueous alkaline solution is employed in an amount five to six times the stoichiometric amount of 1,2,3,4-tetrahydro-4-oxocarbazole.

4. Process as claimed in claim 1 wherein the aqueous alkaline solution is approximately 2 N.

5. Process as claimed in claim 1 wherein the aqueous alkaline solution is an aqueous potassium hydroxide solution.

6. Process as claimed in claim 1 wherein the reaction is carried out in an inert gas atmosphere.

7. Process as claimed in claim 6 wherein the inert gas is nitrogen.

* * * * *